(12) United States Patent
Argraves

(10) Patent No.: US 6,298,850 B1
(45) Date of Patent: Oct. 9, 2001

(54) NASAL CANNULA ASSEMBLY AND SECURING DEVICE

(76) Inventor: Gloria Jean Argraves, R.R. #1 Box 52A, Princeton, ME (US) 04668

( * ) Notice: Subject to any disclaimer, the term of this patent is extended or adjusted under 35 U.S.C. 154(b) by 0 days.

(21) Appl. No.: 09/368,751

(22) Filed: Aug. 5, 1999

(51) Int. Cl.[7] .................................................. A61M 16/00
(52) U.S. Cl. ............................. 128/207.17; 128/207.18; 128/207.14; 128/204.12; 128/202.27
(58) Field of Search .................... 128/207.17, 207.18, 128/DIG. 26, 206.27, 202.27, 201.15, 201.19, 200.26, 204.11, 204.12, 207.14

(56) References Cited

U.S. PATENT DOCUMENTS

| | | |
|---|---|---|
| 4,106,505 | 8/1978 | Salter et al. . |
| 4,249,529 * | 2/1981 | Nestor et al. ................... 128/207.17 |
| 4,406,283 * | 9/1983 | Bir .................................. 128/207.18 |
| 4,422,456 | 12/1983 | Tiep . |
| 4,699,139 * | 10/1987 | Marshall et al. ................ 128/207.18 |
| 4,821,736 | 4/1989 | Watson . |
| 4,836,200 | 6/1989 | Clark . |
| 5,087,118 * | 2/1992 | Gill ...................................... 351/156 |
| 5,117,818 * | 6/1992 | Palfy ................................ 128/204.11 |
| 5,271,391 * | 12/1993 | Graves ............................ 128/207.18 |
| 5,305,742 | 4/1994 | Styers et al. . |
| 5,438,979 * | 8/1995 | Johnson, Jr. et al. .......... 128/207.18 |
| 5,533,506 | 7/1996 | Wood . |
| 5,636,630 | 6/1997 | Miller et al. . |
| 5,645,058 * | 7/1997 | Odom .............................. 128/207.18 |
| 5,704,916 * | 1/1998 | Byrd ................................ 128/207.17 |
| 5,727,580 * | 3/1998 | Patterson .......................... 134/115 R |

OTHER PUBLICATIONS

Advertising, apparently in Sep. 1992 Journal for Respiratory Care Practitioners, published by Allied Health Care, Div. of Curant Communications, Marina Del Ray CA, for a "new Dale Oxygen Cannula Support", (best available copy).

* cited by examiner

Primary Examiner—John G. Weiss
Assistant Examiner—V. Srivastava
(74) Attorney, Agent, or Firm—Shalom Wertsberger; Saltamar Innovations

(57) ABSTRACT

A device for securing a nasal cannula to a patient's head is disclosed. The device utilizes a thin round elastic band placed behind the patient's head and is attached to the cannula gas supply tube by cord couplers. The cord couplers are slidably attached to the gas supply tubes to allow fast and easy adjustment to size. The device is light, comfortable, inexpensive and simple to use. It prevents painful hair entanglement and allows single handed deployment and adjustment of a nasal cannula, while affording secured placement of the cannula during patient movement or sleep. Additionally, a nosepiece having a downwardly oriented U shape or arcuate fold in its center portion is disclose to prevent the cannula nosepiece from exerting excessive pressure against the patient's septum. A method of use is also disclosed.

20 Claims, 3 Drawing Sheets

NASAL CANNULA ASSEMBLY AND SECURING DEVICE

FIELD OF THE INVENTION

This invention relates in general to nasal cannulas, and more particularly to a securing a nasal cannula at a desired position on a patient and an improved nosepiece.

BACKGROUND

Nasal cannulas are well known in the art, and are characterized by U.S. Pat. No. 4,106,505 to Salter et al. Cannulas are frequently used to alleviate respiratory distress due to many types of respiratory medical conditions by supplying an oxygen enriched air stream to a patient. Often wearing the cannula on a 24 hour a day basis is a medical necessity. The use of a nasal cannula allows the patient freedom of movement and activity, while being unobtrusive as compared to the larger and bulkier facemasks.

A nasal cannula comprises essentially a nasal assembly, or nosepiece, with a hollow main body having two directed orifices near or in a patient nostrils. The gas is supplied to the main body that acts as a distributing manifold. Typically, the orifices are placed at the end of nasal extension tubes extending upwardly from a main body portion and in communication with the main body. Commonly two gas supply tubes are attached to the cannula nosepiece, that is held in place by extending the gas supply tubes from the patient's nasal area behind the patient's ears. The flexible tubes are bent downward behind the ears to run generally along the jaw area, and are held in place by an adjustable slip loop or a cinch tightened below the chin to hold the nosepiece in place. Oxygen or other gas flows through the tube to the two orifices, and the gas is mixed with the air stream of the patient air intake.

While being one of the most convenient methods known to date for supplying a patient with a gas enriched environment, nasal cannulas suffer a major drawback: the positioning of the tubes around the ears for support is uncomfortable and is prone to falling off the patient's face. Additionally, it causes the patient chaffing and pain. Patients regularly find that body movement, especially during sleep, causes the cannula to dislocate, depriving the patient of the needed oxygen enrichment. Accidental removal of the cannula often causes severe discomfort to the patient and in certain cases may even be life threatening.

U.S. Pat. Nos. 5,636,630 to Miller et al., 4,836,200 to Clark, and 4,422,456 to Tiep, all attempt to solve this problem. Miller et al. discloses running the tubes behind the patient head and utilizing a coupling portion contacting the back of the head, with the gas conduits passing in criss-cross manner behind the head. This arrangement suffers from several disadvantages, major amongst them is the location of both oxygen tubes behind the patient's head where they may be blocked if the head is resting thereupon. Additionally, placement of tubes behind the head is often uncomfortable to the patient.

The Clark patent utilizes a pressure-fastening strap adapted to go over the top of a user's head, onto which the flexible tubes are attached. Clark also discloses and teaches away from a strap wrapped completely around the head, with separate attachment means for the flexible tubes. Clark's preferred implementation is less desirable since the strap may slide over the head of the user and is liable to entangle with the patient's hair.

Tiep's patent discloses means for supporting the cannula in place by an elastic band that is adjustably connected to two holders each located on one of the conduits or flexible tubes. Each of the holders includes a band fitting around the conduit and in frictional engagement with it, and a tab attached to the band so as to extend generally along the conduit. An elastic band extending behind the patient's head is secured to the tab by being threaded through openings within the tab. Two problems arise from the Tiep patent: First, a structure according to Tiep requires threading adjustment of the elastic band. This is time consuming, and when done on a patient head also runs the risk of entanglement in the patient's hair. This problem is especially significant to nurses in a hospital where time is often of the essence. Additionally, an elastic band, being flat in cross section, runs the risk of entanglement in the patient's hair.

In use, typically the nosepiece of a cannula is placed against the nasal septum, and tension is applied against it to secure the nosepiece in place. The tension exerted against the septum causes sever discomfort to some patients, especially during respiratory or medical conditions such as allergies and cold. Soft and flexible materials are commonly used in the construction of nasal cannulas, but the pressure on the soft tissue surrounding the nasal septum stems from the tension necessary to hold the nasal cannula in place.

It is clear therefore that a need exists for a device to secure a nasal to a patient's head in a light, inexpensive, and effective manner, and doing so in a manner that will be unobtrusive to the patient. Additionally, a better solution is needed for providing user comfort in the nasal septum area as described above. The current invention discloses such a device and method for its use.

SUMMARY

It is therefore an objective of the current invention to provide means for securing a gas supply cannula to a patient wearing it so as to insure continuous and uninterrupted supply of oxygen as needed, thus avoiding the discomfort stemming from having to place gas supply tubing behind the patient's ears, or a tight cinch under the patient's neck.

The current invention is based on the discovery that using a flexible elastic cord 40 of generally round cross section and having a relatively small diameter, preferably no larger than one or two millimeters, is uniquely suitable for securing the cannula with only minor inconvenience to the patient. It was found that the use of such round, small diameter elastic cord in combination with other aspects of the current invention, solves the problem of user comfort and hair entanglement, all while ensuring a secure method of affixing the nasal cannula in place. It is also an object of this invention to provide for easy, fast, and single-handed adjustment of the cannula in place to permit easy adjustment for different head dimensions. To that end, a cord coupler 30 and 35 is also disclosed herein. The cord coupler is in slidable engagement with the flexible gas supply tubes 20 and 25 supplying oxygen to the cannula nosepiece 10. The elastic cord 40 is attached to the cord couplers 30 and 35, that in turn couples the cord to the gas supply tubes 20 and 25. In the preferred implementation, two cord couplers are utilized, made of flexible tubing with an inner diameter slightly larger than the outer diameter of the gas supply tubes. The cord is attached to the cord couplers in any convenient manner. The simplest form of a cord coupler comprises a loop formed in the cord around the gas supply tube and tied or otherwise bonded against it in a slidable engagement.

In use, the first end of the cord is coupled to one of the two gas supply tubes, and the second end of the cord is coupled to the other gas supply tube. At least one end is coupled by means of a cord coupler as described above. By placing the nosepiece next to a patient's nostrils, and by placing the elastic cord behind the patient's head so it rests against the back portion of the head, the nasal cannula is secured in place. The gas supply flexible tubes are extended towards the patient's ears. At least one of the cord couplers is slidably adjusted forward towards the nosepiece in order to achieve a comfortable fit of the cannula while securing it in place. Thus the cord couplers support the flexible gas supply tubes and the tubes rest on opposite sides of the patient's face, and may be bent downwardly behind the cord couplers and thus avoid the patient's ears altogether. The gas supply tubes generally run down along the jaw area to a meeting point under the patient's neck, but without requiring a cinch to hold them tight against the neck. However any convenient routing of the gas tubes is acceptable since only the portion of the tube between the cord coupler and the nosepiece take part in securing the nosepiece in place.

It is yet another object of the current invention to relieve the pressure exerted by the nosepiece main body on the nasal septum area. The invention achieves this goal by a septal pressure relief 90 comprising a valley portion or depression in the nosepiece main body. The valley portion is formed or otherwise introduced in the central segment 15 of the main body interposed the two orifices or nasal extension tubes 13 and 17. The valley may be in the form of a bend, a notch, a curve, v or square shaped notch, a downwardly oriented, generally U shaped depression, or any other shaped depression in the upper surface of the nosepiece main body, causing the main body to deflect away from the patient's septum. The valley avoids or minimizes direct contact between the main body and the nasal septal area. The tension is thus transferred to the softer tissue of the lower portion of the outer nostril walls. Since the outer nostril wall is not supported by a bone, it offers a more convenient support for the nosepiece. Clearly, the septal pressure relief and the securing device disclosed herein may be utilized in combination or separately in a nasal cannula.

The cannula securing means disclosed herein may be made as an attachment to an already manufactured oxygen supply nasal cannula or may be embedded into the cannula manufacturing process.

DETAILED DESCRIPTION

Figure 1:
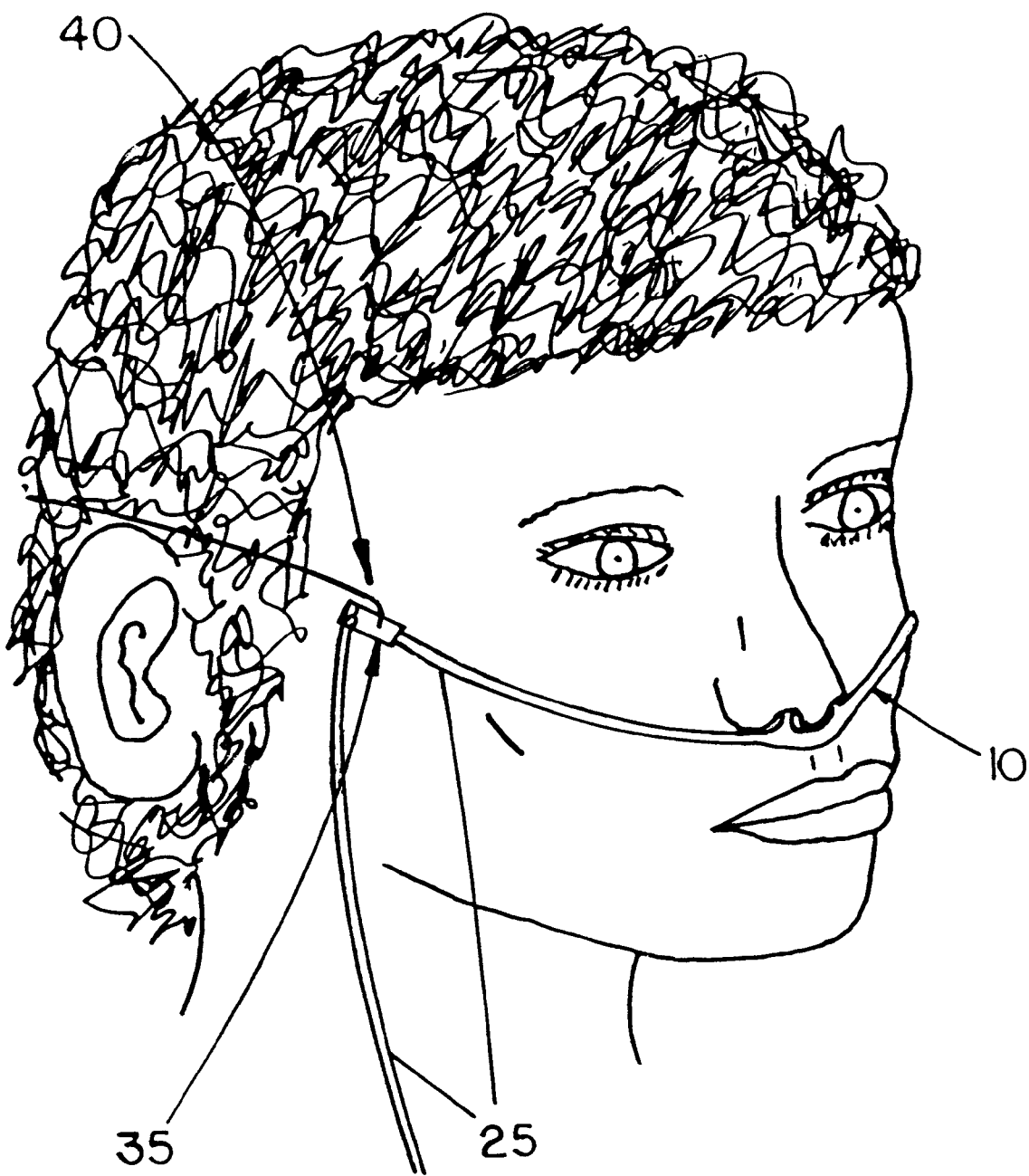
FIG. 1 depicts a perspective view of a patient using a preferred implementation of the current invention.
Figure 2:
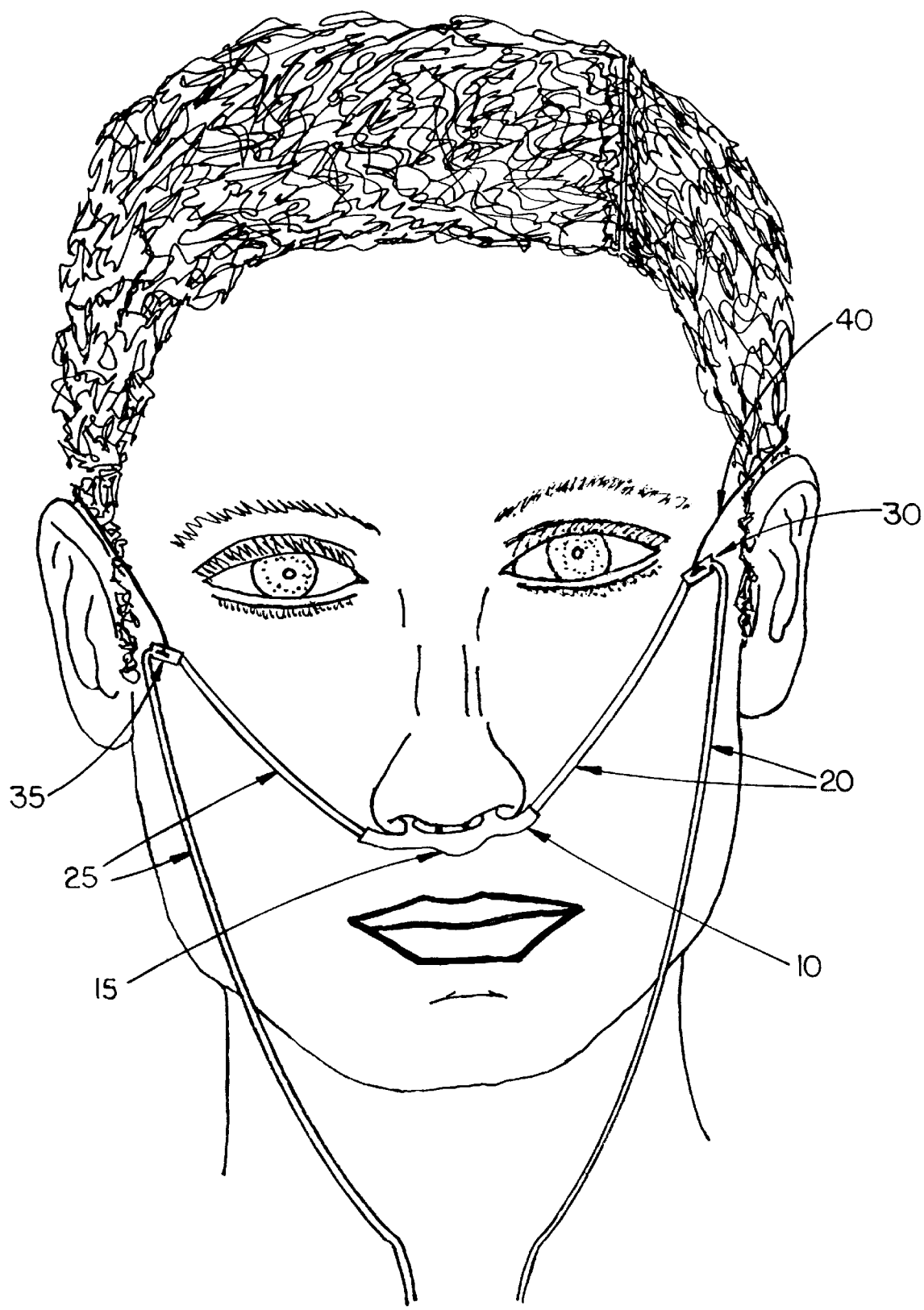
FIG. 2 depicts a frontal view of a patient's head while using the invention and showing a preferred implementation wherein the tubes run anteriorily to patient ears.

In the preferred implementation the invention utilizes a round elastic cord attached to cord couplers 30 and 35. The elastic cord 40 may be of round or elliptical construction but experiments have shown the generally round cross section to be the preferred implementation. The most preferred cord is composed of rubber or other elastic polymer, and is approximately one (1) millimeter in diameter, since this size has proven to be least prone to entanglement in the patient's hair while producing sufficient mechanical strength. While larger diameter may work as well, a cord diameter above approximately seven millimeters suffers from some or all of the disadvantages of prior attempted solutions. In general, any cord having a diameter less than three millimeters is preferred for practicing the invention. In one preferred implementation, the cord 40 is approximately 30 centimeters in length, however this dimension may be varied to any desired length to fit varying head sizes.

The preferred implementation uses two slidable cord couplers, 30 and 35 respectively, however only one may be used if so desired for reduced cost. For clarity this disclosure will concentrate on a single cord coupler, 30 with an understanding that a similar cord coupler 35 may correspondingly be used on the opposite side of the patient's head.

The most important deciding criteria demanded from the cord coupler 30 being a sliding attachment of sufficient friction to hold the cannula nasal assembly 10 in place, while allowing fast and easy adjustment of the elastic cord 40. Other preferable requirements from the cord coupler are that it will be easily adjustable along the length of the gas supply tube 20, and be able to exert enough force thereupon to maintain positive engagement so as to keep the nosepiece 10 in place; without choking the gas supply tube in a manner that may restrict gas flow therein.

The cord coupler 30 in the preferred implementation is constructed substantially of a cord coupler tube: a short piece of flexible tubing of about ten to fifteen (10–15) millimeter in length, however this length may be varied at will. The internal diameter of the cord coupler tube is large enough to fit over the cannula gas supply tube 20, which is at least partially disposed within the cord coupler tube. In the preferred implementation, the elastic cord 40 is passed through a hole 32 or an opening in the sidewall of the cord coupler tube. The elastic cord is held in place by an enlargement of the cord diameter so as to prevent it from sliding out of the hole. Such enlargement may be made by melting the cord end, glue, a bid, a knot tied near the cord's end, or any other conventional measure. Alternatively glue, heat welding, or any other convenient technique may be used to attach the elastic cord 40 to the cord coupler 30. Preferably, the cord couplers and the elastic cord are attached to the nasal cannula during manufacturing, but it may also be fitted to an existing cannula.

It will be clear to a person skilled in the art that other implementations of the cord coupler 30 are possible without detracting from the spirit of the invention. Such other implementations include, but are not limited to, a cylinder, a cloth loop, a clip adapted to accept the gas supply tube without pinching it, a molded cylindrical tube holder, or a loop formed in the elastic cord 40 around the cannula gas supply tube 20, and forming a slidable attachment with it. It should be mentioned however that any such attachment method of the elastic to the gas supply tube should be made with consideration towards the aims and requirements mentioned above.

Figure 4:
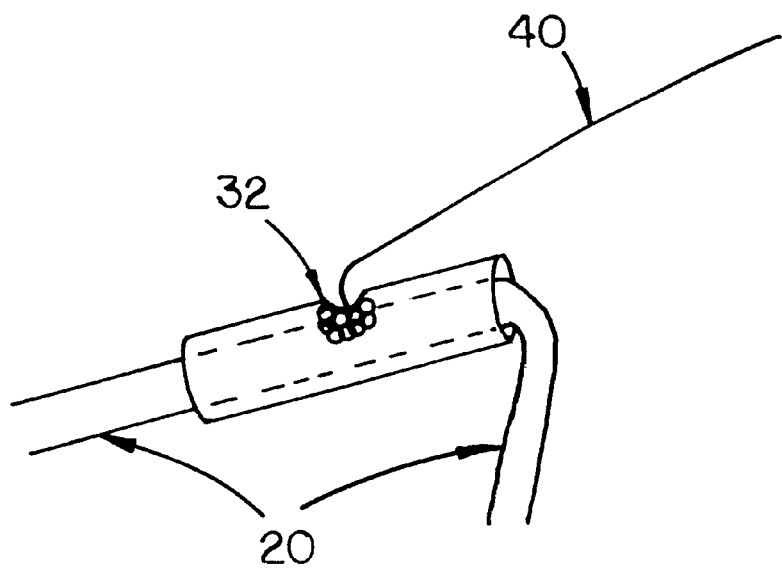
FIG. 4 shows a preferred implementation of a cord coupler in accordance with the current invention.

The described method shown in FIG. 4, in which the elastic cord 40 is passed through a hole 32 in the cord coupler tube sidewall with the cord's end being enlarged, has an added advantage. This method reduces the risk of choking the tube while supplying pliable pressure of the gas supply tube against the opposite inner side of the cord coupler tube sidewall.

While the preferred embodiment utilizes two slidable cord couplers 30 and 35, one end of the cord may be permanently attached to one gas supply tube, while the other end having a cord coupler to adjust the elastic cord to size. Such arrangement however, is considered less comfortable to the patient.

In use, the cannula is placed generally with the nosepiece 10 near the patient's nostrils, and the elastic cord 40 is placed behind the patient's head. The two slidable cord couplers 30 and 35 are than slide forward along the gas supply tubes 20 and 25 towards the nosepiece to provide the desired tension and to secure the cannula in place.

Figure 3:
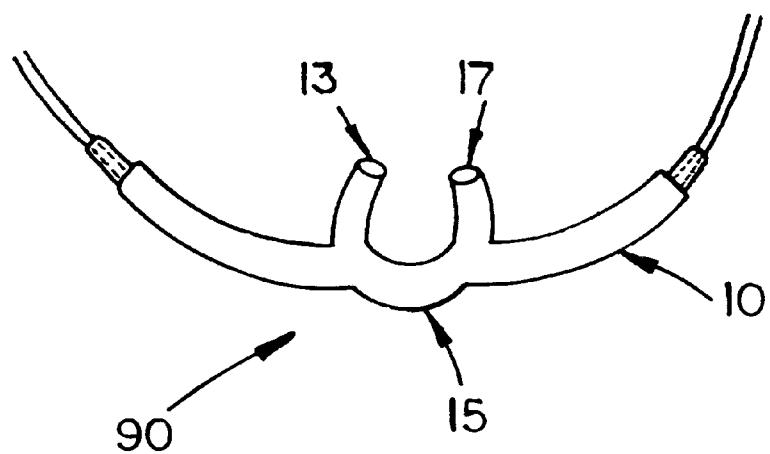
FIG. 3 depicts a nasal cannula nosepiece with septal pressure relief in accordance with a preferred implementation of the invention.

The preferred implementation also includes an improved nosepiece 10 having a septal pressure relief. The septal pressure relief, generally designated numeral 90 in FIG. 3, comprises primarily of a downwardly extending valley portion formed in the central segment 15 of the nosepiece 10. The valley portion comprises a generally U shaped, downwardly arcuate fold segment, formed or molded within the central segment of the main body of the cannula nosepiece and preferably integral thereto. The arcuate fold segment is interposed between the nostril extension tubes 13 and 17, and is formed hollow to allow the nosepiece main body to continue functioning as a gas distribution manifold. The downward arcuation of the segment allow transfer of most if not all of the tension normally exerted on the patient nasal septum area to the lower portion of the outer nostril walls, and to the patient's nasalabidial area.

While there have been described what are at present considered to be the preferred embodiments of this invention, it will be obvious to those skilled in the art that various changes and modifications may be made therein without departing from the invention and it is, therefore, aimed to cover all such changes and modifications as fall within the true spirit and scope of the invention, for which Letters Patent is applied.

What is claimed is:

1. A nasal cannula securing device, comprising:
   a nasal cannula nosepiece connected to a first and a second gas supply tubes;
   a cord coupler for slidingly supporting the first gas supply tube;
   an elastic cord having a first end and a second end, the first end being coupled to the cord coupler and the second end adapted to be coupled to the second gas supply tube; and
   wherein the elastic cord of a substantially round cross section with a diameter of smaller than seven millimeters.

2. The device of claim 1, further comprising a second cord coupler for slidingly supporting the second gas supply tube, the second end of the elastic cord is attached to the second cord coupler for slidingly supporting the second gas supply tube.

3. The device of claim 1, wherein the cord coupler is cylindrical in shape and a portion of the gas supply tube is slidingly supported within the cylindrical shape of the cord coupler.

4. The device of claim 1, wherein the cord coupler is tubular in shape and a portion of the gas supply tube is slidingly supported within the tubular shape of the cord coupler.

5. The device of claim 4, further comprising a second cord coupler for slidingly supporting the second gas supply tube, the second cord coupler having a tubular shape for slidingly supporting a portion of the second gas supply tube within the tubular shape.

6. The device of claim 4, wherein the cord coupler is flexible.

7. The device of claim 3, wherein the cord coupler is flexible.

8. The device of claim 1, wherein the elastic cord comprises a loop formed at the second end for slidingly supporting the second gas supply tube.

9. The device of claim 2, wherein the elastic cord having a diameter less than three millimeters.

10. The device of claim 2, wherein the elastic cord having a diameter of approximately one millimeters.

11. The device of claim 1, wherein the nosepiece further comprising a downwardly arcuated hollow central segment.

12. A method for securing a nasal cannula having two gas supply flexible tubes to patient's head comprising:
    placing a nasal cannula nosepiece adjacent to a patient's nostrils;
    placing an elastic cord having a substantially rounded cross section behind the back portion of a patient's head; and
    adjusting a cord coupler attached to a first end of the elastic cord along the first gas supply tube.

13. The method of claim 12, comprising the elastic cord having a diameter less than three millimeter.

14. The method of claim 12, wherein the first end of the elastic cord is slidingly attached to the first gas supply tube.

15. The method of claim 12, comprising the elastic cord having a diameter less than seven millimeter.

16. The method of claim 12, wherein the nosepiece having a downwardly arcuated hollow central segment.

17. The method of claim 13, wherein the nosepiece having a downwardly arcuated hollow central segment.

18. A nasal cannula securing device, comprising:
    a nasal cannula nosepiece connected to a first and a second gas supply tubes;
    a first cord coupler for slidingly supporting the first gas supply tube and a second cord coupler for slidingly attaching the second gas supply tube; and
    an elastic cord having a first end and a second end, the first end being coupled to the first cord coupler and the second end adapted to be coupled to the second cord coupler;
    wherein the elastic cord of a substantially round cross section with a diameter of smaller than seven millimeters.

19. The device of claim 18, wherein the nosepiece further comprising a downwardly arcuated hollow central segment.

20. The device of claim 18, wherein the elastic cord having a diameter smaller than three millimeters.

* * * * *